US006309635B1

(12) United States Patent
Ingber et al.

(10) Patent No.: US 6,309,635 B1
(45) Date of Patent: Oct. 30, 2001

(54) SEEDING PARENCHYMAL CELLS INTO COMPRESSION RESISTANT POROUS SCAFFOLD AFTER VASCULARIZING IN VIVO

(75) Inventors: Donald E. Ingber, Boston; Robert S. Langer, Newton; Joseph P. Vacanti, Winchester, all of MA (US)

(73) Assignees: Children's Medical Center Corp., Boston; Massachusetts Institute of Technology, Cambridge, both of MA (US)

( * ) Notice: Subject to any disclaimer, the term of this patent is extended or adjusted under 35 U.S.C. 154(b) by 0 days.

(21) Appl. No.: 08/345,217

(22) Filed: Nov. 28, 1994

Related U.S. Application Data

(63) Continuation of application No. 08/065,452, filed on May 21, 1993, now abandoned, which is a continuation of application No. 07/785,021, filed on Oct. 30, 1991, now abandoned, which is a continuation-in-part of application No. 07/401,640, filed on Aug. 30, 1999, now abandoned, which is a continuation of application No. 06/933,018, filed on Nov. 20, 1986, now abandoned, application No. 08/345,217, filed on Apr. 1, 1991, now abandoned, which is a continuation-in-part of application No. 07/679,177, filed on Mar. 26, 1991, now abandoned, which is a continuation of application No. 07/401,648, filed on Aug. 30, 1989, now abandoned, which is a continuation of application No. 07/123,579, filed on Nov. 20, 1987, now abandoned, which is a continuation-in-part of application No. 07/680,608, filed on Apr. 1, 1991, now abandoned, which is a continuation of application No. 07/343,158, filed on Apr. 25, 1989, now abandoned, application No. 08/345,217, which is a continuation-in-part of application No. 07/514,171, filed on Apr. 25, 1990, now abandoned, which is a continuation-in-part of application No. 07/343,158, which is a continuation-in-part of application No. 07/123,579, which is a continuation-in-part of application No. 06/933,018.

(51) Int. Cl.[7] .......................... A01N 63/00; A61F 2/00; C12N 11/08; C12N 5/06; C12N 5/08

(52) U.S. Cl. ................. 424/93.7; 424/423; 424/486; 435/177; 435/180; 435/395; 435/396; 435/398; 435/402

(58) Field of Search ................. 435/177, 180, 435/240.21, 240.23, 240.243, 395, 396, 398, 402; 524/24, 421; 436/823; 424/422, 423, 456, 19, 93.7, 486; 423/11, 12, 13

(56) References Cited

U.S. PATENT DOCUMENTS

| 2,609,347 | 9/1952 | Wilson | 521/87 |
|---|---|---|---|
| 2,653,917 | 9/1953 | Hammon | 521/136 |
| 2,659,935 | 11/1953 | Hammon | 264/321 |
| 2,664,366 | 12/1953 | Wilson | 15/244.4 |
| 2,664,367 | 12/1953 | Wilson | 15/244.4 |
| 2,846,407 | 8/1958 | Wilson | 521/53 |
| 3,826,241 | 7/1974 | Bucalo | 128/1 R |
| 3,880,991 | 4/1975 | Yolles | 424/22 |
| 3,883,393 | 5/1975 | Knazck et al. | 195/1.8 |
| 3,902,497 | 9/1975 | Casey | 128/296 |
| 3,949,073 | 4/1976 | Daniels | 424/177 |
| 3,960,150 | 6/1976 | Hussain et al. | 128/260 |

(List continued on next page.)

FOREIGN PATENT DOCUMENTS

| 2853614 | 7/1979 | (DE) . |
|---|---|---|
| 0226061 | 11/1986 | (EP) . |
| 0282746 | 9/1988 | (EP) . |
| 0339607 | 11/1989 | (EP) . |
| 62011459 | 1/1987 | (JP) . |
| 63074498 | 4/1988 | (JP) . |
| 63196273 | 8/1988 | (JP) . |
| 63196595 | 8/1988 | (JP) . |
| WO 87/06120 | 4/1987 | (WO) . |
| WO 88/03785 | 6/1988 | (WO) . |
| WO 89/00413 | 7/1988 | (WO) . |
| WO 8907944 | 9/1989 | (WO) . |
| WO 9012603 | 11/1990 | (WO) . |
| WO 9012604 | 11/1990 | (WO) . |

OTHER PUBLICATIONS

Lesson et al pp. 86, 87, & 114 Histology $3^{rd}$ ed W.B. Saunder Co 1976.*

Structure & Function in Man W.B. Saunders Co 1982 pp. 85–88, 383,384 , 484 & 413.*

Naji et al Surgery 86:218–226 1979.*

Thunoff et al Urology 21:155–158 1983.*

Alberts, et al., *Molecular Biology of the Cell*, 893 and 894 (1983).

(List continued on next page.)

*Primary Examiner*—David M. Naff
(74) *Attorney, Agent, or Firm*—Clark & Elbing, LLP; Timothy J. Douros

(57) ABSTRACT

A method is provided whereby cells having a desired function are seeded on and into biocompatible, biodegradable or non-degradable porous polymer scaffolding matrix, previously implanted in a patient and infiltrated with blood vessels and connective tissue, to produce a functional organ equivalent. The resulting organoid is a chimera formed of parenchymal elements of the donated tissue and vascular and matrix elements of the host. The matrix should be compression resistant and a non-toxic, porous template for vascular ingrowth. The pore size, usually between approximately 100 and 300 microns, should allow vascular and connective tissue ingrowth throughout approximately 10 to 90% of the matrix, and the injection of cells such as hepatocytes without damage to the cells or patient. The introduced cells attach to the connective tissue and are fed by the blood vessels. Immediately prior to matrix implantation portacaval shunts can be created to provide trophic stimulatory factors to the implanted matrix to enhance replication and function.

16 Claims, 3 Drawing Sheets

U.S. PATENT DOCUMENTS

| | | | |
|---|---|---|---|
| 3,974,526 | 8/1976 | Darkik et al. | 3/1.4 |
| 3,992,725 | 11/1976 | Homsy | 3/1 |
| 4,026,304 | 5/1977 | Levy | 128/419 F |
| 4,060,081 | 11/1977 | Yannas et al. | 128/156 |
| 4,069,307 | 1/1978 | Higuchi et al. | 424/22 |
| 4,137,921 | 2/1979 | Okuzumi | 128/335.5 |
| 4,141,087 | 2/1979 | Shalaby et al. | 3/1 |
| 4,144,126 | 3/1979 | Burbidge | 195/1.1 |
| 4,186,448 | 2/1980 | Brekke | 3/1.9 |
| 4,192,827 | 3/1980 | Mueller et al. | 525/123 |
| 4,205,399 | 6/1980 | Shalaby et al. | 3/1 |
| 4,228,243 | 10/1980 | Iizuka | 435/285 |
| 4,239,664 | 12/1980 | Teng et al. | 260/17.4 |
| 4,243,775 | 1/1981 | Rosensaft et al. | 525/415 |
| 4,277,582 | 7/1981 | Mueller et al. | 525/421 |
| 4,280,954 | 7/1981 | Yannas et al. | 260/123.7 |
| 4,304,591 | 12/1981 | Mueller et al. | 71/93 |
| 4,304,866 | 12/1981 | Green et al. | 424/574 |
| 4,328,204 | 5/1982 | Wasserman | 424/19 |
| 4,347,847 | 9/1982 | Usher | 128/334 |
| 4,348,329 | 9/1982 | Chapman | 260/403 |
| 4,356,261 | 10/1982 | Kuettner | 435/68 |
| 4,391,797 | 7/1983 | Folkman et al. | 424/19 |
| 4,416,986 | 11/1983 | Markus et al. | 435/68 |
| 4,427,808 | 1/1984 | Stöl et al. | 524/24 |
| 4,431,428 | 2/1984 | Schmer | 604/897 |
| 4,438,198 | 3/1984 | Schmer | 435/178 |
| 4,439,152 | 3/1984 | Small | 433/173 |
| 4,444,887 | 4/1984 | Hoffmann | 435/240 |
| 4,446,234 | 5/1984 | Russo et al. | 435/29 |
| 4,450,150 | 5/1984 | Sidman | 424/1.1 |
| 4,456,687 | 6/1984 | Green | 435/240 |
| 4,458,678 | 7/1984 | Yannas et al. | 128/155 |
| 4,485,096 | 11/1984 | Bell | 424/95 |
| 4,485,097 | 11/1984 | Bell | 424/95 |
| 4,489,056 | 12/1984 | Himmelstein | 424/22 |
| 4,505,266 | 3/1985 | Yannas et al. | 128/1 |
| 4,520,821 | 6/1985 | Schmidt et al. | 128/334 |
| 4,528,265 | 7/1985 | Becker | 435/172.1 |
| 4,544,516 | 10/1985 | Hughes et al. | 264/108 |
| 4,545,082 | 10/1985 | Hood | 623/1 |
| 4,546,500 | 10/1985 | Bell | 623/1 |
| 4,553,272 | 11/1985 | Mears | 623/1 |
| 4,559,304 | 12/1985 | Kasai et al. | 435/240 |
| 4,563,490 | 1/1986 | Stöl et al. | 524/24 |
| 4,576,608 | 3/1986 | Homsy | 3/1 |
| 4,609,551 | 9/1986 | Caplan et al. | 424/95 |
| 4,637,931 | 1/1987 | Schmitz | 424/73 |
| 4,642,120 | 2/1987 | Nevo et al. | 623/16 |
| 4,645,669 | 2/1987 | Reid | 424/95 |
| 4,675,189 | 6/1987 | Kent et al. | 424/90 |
| 4,681,763 | 7/1987 | Nathanson et al. | 424/95 |
| 4,713,070 | 12/1987 | Mano | 623/1 |
| 4,721,096 | 1/1988 | Naughton et al. | 128/1 R |
| 4,757,017 | 7/1988 | Cheung | 435/240.33 |
| 4,757,128 | 7/1988 | Domb | 528/271 |
| 4,778,749 | 10/1988 | Vashington et al. | 435/2 |
| 4,846,835 | 7/1989 | Grande | 623/11 |
| 4,853,324 | 8/1989 | Viles | 435/2 |
| 4,868,121 | 9/1989 | Scharp et al. | 435/268 |
| 4,891,225 | 1/1990 | Langer et al. | 424/428 |
| 4,963,489 | 10/1990 | Naughton et al. | 435/240.1 |
| 4,988,761 | 1/1991 | Ikada et al. | 524/557 |
| 5,032,508 | 7/1991 | Naughton et al. | 435/32 |
| 5,041,138 * | 8/1991 | Vacanti et al. | 623/16 |
| 5,514,378 * | 5/1996 | Mikos et al. | 424/425 |
| 5,567,612 * | 10/1996 | Vacanti et al. | 435/240.23 |
| 5,736,372 * | 4/1998 | Vacanti et al. | 435/180 |

OTHER PUBLICATIONS

Anderson, David J., et al., Caltech Biology (1987).

Anderson, Kathryn D., et al., "Gene Expression in Implanted Rat Hepatocytes Following Retroviral–Mediated Gene Transfer," *Somatic Cell and Molecular Genetics*, vol. 15, pp. 215–227 (1989).

Backlund, Erik–Olof, et al., "Toward a Transplantation Therapy in Parkinson's Disease," *Annals of the N.Y. Academy of Science*, vol. 495, pp. 658–673 (1987).

Bazeed, et al., "New Treatment for Urethral Strictures," Urology 21(1), 53–57 (1983).

Bazeed, et al., "New Surgical Procedure for Management of Peyronie Disease," Urology 21(5), 501–504 (1983).

Ben–Ze'ev, A., et al., "Cell–Cell and Cell–Matrix Interactions Differentially Regulate the Expression of Hepatic and Cytoskeletal Genes in Primary Cultures of Rat Hepatocytes," *Proc. Natl. Acad. Sci, USA* vol. 85, pp. 2161–2165 (Apr. 1988).

Berrino, Pietro, et al., "Surgical Correction of Breast Deformities Following Long–Lasting Complications of Polyurethane–Covered Implants," *Ann. Plast. Surg.*, 24:481 (1990).

Biers, Elizabeth, "Organogensis' Human Artery Equivalent May Revolutionize Vascular Grafts," Genetic Engineering News, (Nov.–Dec. 1987).

Bissell, D. Montgomery, et al., "Interactions of Rat Hepatocytes with Type IV Collagen, Fibronectin and Laminin Matrices, Distinct Matrix–Controlled Modes of Attachment and Spreading," *European Journal of Cell Biology* 40, 72–78 (1986).

Bissell, D.M., et al., "Support of Cultured Hepatocytes by a Laminin–Rich Gel, Evidence of a Functionally Significant Subendothelial Matrix in Normal Rat Liver," *J. Clin. Invest.*, vol. 79, pp. 801–812 (Mar. 1987).

Bissell, D.M., et al., "The Role of Extracellular Matrix in Normal Liver," Scand. J. Gastroenterol, 23:107 (1988).

Björklund, A., *Annals of the N.Y. Academy of Science*, vol. 495, pp. 676–686 (1987).

Bohn, M.C., et al., "Arenal Medulla Grafts Enhance Recovery of Striatal Dopaminergic Fibers," Science 237(4817):913–6 (Aug. 21, 1987).

"Brain Graft Seeks to Relieve Huntington Disease Patient," The New York Times, (Mar. 4, 1988).

Brown, Norman, "Fibrin–Collagen Nerve Repair Device," Inventors: Russ Griffiths, Larry Stensaas and Ken Horch, Letter dated May 10, 1988.

Burke, "The Effects of the Configuration of an Artificial Extracellular Matrix on the Development of a Functional Dermis," *The Role of Extracellular Matrix in Development* 351–355 (Alan R. Liss, Inc., NY 1984).

Children's Hospital (The), Department of Nursing, Division 5, "Liver Transplantation," (May 1984).

Chuang, Vincent P., et al., "Sheath Needle for Liver Biopsy in High–Risk Patients," *RSNA* pp. 261–262 (1988).

Collier, T.J., et al., "Norepinephrine Deficiency and Behavioral Senescence in Aged Rats: Transplanted Locus Ceruleus Neurons as an Experimental Replacement Therapy," *Annals of the New York Academy of Sciences* vol. 495: 396–403 (New York 1987).

Cosimi, et al., "Transplantation of Skin," Surgical Clinics of N.A. 58(2), 435–451 (Apr. 1978).

Craig, et al., "A Biologic Comparison of Polyglactin 910 and Polyglycolic Acid Synthetic Absorbable Sutures," *Surgery Gynecology & Obstetrics*, vol. 141, No. 1, pp. 1–10 (Jul. 1975).

Culliton, Barbara J., "Gore Tex Organoids and Genetic Drugs," *Science*, vol. 246, pp. 747–749 (Nov. 1989).

da Silva, C.F., et al., "An In Vivo Model to Quantify Motor and Sensory Peripheral Nerve Regeneration Using Bioresorbable Nerve Guide Tubes," *Brain Research*, vol. 342, pp. 307–315 (1985).

Davis, George E., et al., "Human Amnion Membrane Serves as a Substratum for Growing Axons In Vitro and In Vivo," *Science*, vol. 236, pp. 1106–1109 (May 29, 1987).

del Cerro, M., et al. "Retinal Transplants into One Anterior Chamber off the Rat Eye," *Neuroscience* vol. 21(3):707–23 (Jun. 1987).

Doillon, C.J., et al., "Collagen–Based Wound Dressings: Control of the Pore Structure and Morphology," *Journal of Biomedical Materials Research*, vol. 20, pp. 1219–1228 (1986).

Doillon, C.J., et al., "Epidermal Cells Cultured on a Collagen–Based Material," G.W. Bailey, Editor, Proceedings of the 44th Annual Meeting of the Electron Microscopy Society of America, (1986).

Ebata, et al., "Liver Regeneration Utilizing Isolated Hepatocytes Transplanted into the Rat Spleen," *Surg. Forum* 29, 338–340 (1978).

Folkman, Judah, et al., "Angiogenic Factors," *Science*, vol. 235, pp. 442–447 (Jan. 23, 1987).

Fontaine, H., et al., "Optimization Studies on Retroviral Mediated Gene Transfer into Rat Hepatocytes: Implications for Gene Therapy," The Society of University Surgeons, Resident's Program, Cincinnati, Ohio (Feb. 15, 1992).

Freshney, "The Culture Environment: I. Substrate, Gas Phase, and Temperature," *Culture of Animal Cells*, pp. 55–66 (Alan R. Liss, NY 1983).

Gash, D.M., et al., "Amitotic Neuroblastoma Cells Used for Neural Implants in Monkeys," Science, 233(4771):1420–2 (Sep. 26, 1986).

Gash, D.M., "Neural Transplantation: Potential Therapy for Alzheimer's Disease," J. Neural Transm [Suppl] 24:301–8 (1987).

Gilbert, James C., et al., "Cell Transplantation of Genetically Altered Cells on Biodegradable Polymer Scaffolds in Syngeneic Rats," Department of Surgery, The Children's Hospital and Harvard Medical School, Boston, Massachusetts.

Grande, Daniel A., et al., "Healing of Experimentally Produced Lesions in Articular Cartilage Following Chondrocyte Transplantation," *The Anatomical Record* 218:142–148 (1987).

Grande, Daniel A., et al., "The Repair of Experimentally Produced Defects in Rabbit Articular Cartilage by Autologous Chondrocyte Transplantation," (May 11, 1988).

Groth, et al., "Correction of Hyperbillrubinemia in the Glucuronyltransferase–Deficient Rat by Intraportal Hepatocyte Transplantation," *Transplant. Proc.* 9, 313–316 (1977).

Harris, A.K., et al., "Silicone Rubber Substrate: A New Wrinkle in the Study of Cell Locomotion," Science (Wash, D.C.) 208:177–179 (1980).

Henry, E.W., et al., "Nerve Regeneration Through Biodegradable Polyester Tubes," Exp. Neurol, 90(3):652–76 (Dec. 1985).

Inaber, D.E., et al., "Cells as Tensegrity Structures: Architectural Regulation of Histodifferentiation by Physical Forces Transduced Over Basement Membrane," *Gene Expression During Normal and Malignant Differentiation*, L.C. Andersson, et al., editors, pp. 13–32 (Academic Press, Orlando, FL 1985).

Inaber, et al., "Endothelial Growth Factors and Extracellular Matrix Regulate DNA Synthesis Through Modulation of Cell and Nuclear Expansion," *In Vitro Cellular & Development Biology*, vol. 23, No. 5 pp. 387–394 (May 1987).

Inaber, et al., "Control of Capillary Morphogenesis: A Molecular System of Mechanical Switches," *J. Cell Biol.*, 107:797a (1988).

Inaber, et al., "Mechanochemical Switching Between Growth and Differentiation During Fibroblast Growth Factor–Stimulated Angiogenesis Vitro: Role of Extracellular Matrix," *J. Cell Biol.*, vol. 109, pp. 317–330 (1989).

Inaber, et al., "How Does Extracellular Matrix Control Capillary Morphogenesis?", *Cell*, vol. 58, pp. 803–805 (Sep. 8, 1989).

Inaber, et al., "Growth Control through Fibronectin–Dependent Modulation of Cell Shape," *J. Cell Biol.*, 105:219a (1987).

Jauregui, H.O., et al., "Attachment and Long Term Survival of Adult Rat Hepatocytes in Primary Monolayer Cultures: Comparison of Different Substrata and Tissue Culture Media Formulations," *In Vitro Cellular & Development Biology*, vol. 22, No. 1, pp. 13–22 (Jan. 1986).

Jones, et al., "Degradation of Artificial Tissue Substrates," Cancer Invasion and Metastasis: *Biologic and Therapeutic Aspects*, pp. 177–185 (Raven Press, NY 1984).

Kleinman, H.K., et al. "Use of Extracellular Matrix Components for Cell Culture," Analytical Biochemistry 166, 1–13 (1987).

Kolata, Gina, "Parkinson Procedure: Fervor Turns to Disillusion," *The New York Times*, (Apr. 21, 1988).

Kordower, J.H., et al., "An in Vivo and in Vitro Assessment of Differentiated Neuroblastoma Cells as a Source of Donor Tissue for Transplantation," *Annals of the New York Academy of Sciences*, vol. 495, pp. 606–622 (New York 1987).

Kordower, J.H., et al., "Neuroblastoma Cells in Neural Transplants: A neuroanatomical and Behavioral Analysis," Brain Res., 417(1):85–98 (Aug. 4, 1987).

Kretschmer, et al., "Autotransplantation of Pancreatic Fragments to the Portal Vein and Spleen of Totally Pancreatectomized Dogs," *Ann. Surg.*, 187, 79–86 (1978).

Leong, K.W., et al., "Bioerodible Polyanhydrides as Drug–Carriers Matrices. I: Characterization, Degradation, and Release Characteristics," *Journal of Biomedical Materials Research*, vol. 19, 941–955 (1985).

Letourneau, "Possible Roles for Cell–to–Substratum Adhesion in Neuronal Morphogenesis," *Developmental Biology*, 44, 77–91 (1975).

Lewin, "Cloud over Parkinson's Therapy," *Science*, vol. 240, pp. 390–392, (Apr. 22, 1988).

Lewin, "Disappointing Brain Graft Results," *Science*, pp. 1407, (Jun. 10, 1988).

Li, M.L., et al., "Influence of a Reconstituted Basement Membrane and Its Components on Casein Gene Expression and Secretion in Mouse Mammary Epithelial Cells," *Proc. Natl. Acad. Sci. USA* vol. 84, pp. 136–140 (Jan. 1987).

Macklis, J.D., et al., "Cross–Linked Colagen Surface for Cell Culture that is Stable, Uniform, and Optically Superior to Conventional Surfaces," *In Vitro Cellular & Developmental Biology*, vol. 21, No. 3, part I, pp. 189–194 (Mar. 1985).

Madison, R., et al., "Increased Rate of Peripheral Nerve Regeneration Using Bioresorbable Nerve Guides and a Laminin–Containing Gel," *Exp Neurol*, 88(3):767–72 (Jun. 1985).

Madison, R., et al., "Nontoxic Nerve Guide Tubes Support Neovascular Growth in Transected Rat Optic Nerve," Exp Neurol, 86(3):448–61 (Dec. 1984).

Madison, R., et al., "Peripheral Nerve Regeneration With Entubulation Repair: Comparison of Biodegradable Nerve Guides Versus Polyethylene Tubes and the Effects of a Laminin–Containing Gel," *Exp Neurol*, 95(2):387–90 (Feb. 1987).

Marciano, F.F., et al., "Structural and Functional Relationships of Grafted Vasopressin Neurons," *Brain Res.*, 370(2):338–42 (Apr. 9, 1986).

Matas, et al., "Hepatocellular Transplantation for Metabolic Deficiencies: Decrease of Plasma Bilirubin in Gunn Rats," *Science* 192, 892–894 (1976).

Mesnil, et al., "Cell contact but Not Junctional Communication (Dye Coupling) with Biliary Epithelial Cells is Required for Hepatocytes to Maintain Differentiated Functions," *Exper. Cell Res.*, 173 (1987)(524–533.

Michalopoulos, G., et al., "Primary Culture of Parenchymal Liver cells on Collagen Membranes," Exper. Cell. Res. 94 (1975) 70–78.

Millaruelo. Ana I., "Role of Plasminogen Activator and its Inhibitors in Axonal Outgrowth and Regeneration In Vivo," *Caltech Biology*, (1987).

Minato, et al., "Transplantation of Hepatocytes for Treatment of Surgically Induced Acute Hepatic Failure in the Rat," *Eur. Surg. Res.*, vol. 16, pp. 162–169 (1984).

Mito, Michio, et al., "Hepatocellular Transplantation," Department of Surgery, Asahikawa Medical College, 078 4–5 Nishi–Kagura, Asahikawa, Japan.

Mooney, David, et al., "Control of Hepatocyte Function Through Polymer–Substrate Modulation," Thesis Proposal—Department of Chemical Engineering, Masssachusetts Institute of Technology (Sep. 22, 1989).

Mooney, David, et al., "Switching from Differentiation to Growth in Hepatocytes: control by Extracellular Matrix," *J. Cell Phys.* (in press) revised MS #7789.

Mounzer, et al., "Polyglycolic Acid Mesh in Repair of Renal Injury," *Urology* 28(2), 127–130 (1986).

Movitz, David, "Accessory Spleens and Experimental Splenosis Principles of Growth," *The Chicago Medical School Quarterly*, vol. 26, No. 4, pp. 183–187 (Winter–Spring 1967).

Naji, et al., "Successful Islet Transplantation in Spontaneous Diabetes," Surgery 86, 218–226 (1979).

Nastelin, Jennifer Green, "Pancreatic Islet Cell Transplantation: Optimization of Islet Cell Adhesion by Altering Polymer Surface Characteristics," Harvard–M.I.T. Division of Health Sciences and Technology (Feb. 1990).

Notter, M.F., et al., "Neuronal Properties of Monkey Adrenal Medulla In Vitro," Cell Tissue REs, 244(1):69–76 (1986).

Oellrich, R.G., et al., "Biliary Atresia," *Neonatal Network*, pp. 25–30 (Apr. 1987).

Oliwenstein, Lori, "The Power of Plastics," Discover, p. 18 (Dec. 1989).

Omery, Anna, et al., "A Nursing Perspective of the Ethical Issues Surrounding Liver Transplantation," Heart & Lung, vol. 17, No. 6 (Nov. 1988).

Patterson, P.H., et al. "Adrenal Chromaffin Cell–Derived Cholinergic Neurons for Brain Transplants," *Caltech Biology* (1987).

Patterson, P.H., et al. *Caltech Biology*, pp. 199–200 (1987).

Perlow, M.J., "Brain Grafting as a Treatment for Parkinson's Disease," *Neurosurgery*, vol. 20, No. 2, pp. 335–342 (1987).

Pimpl, et al., "Experimentelle Studie zur Frage der Transplantatkonditionierung and Transplantatgröfe Bei Heterotoper Autologer Milztransplantation," *Lagenbecks Archiv.* 37215–36218 (Salzburg 1984).

Pimpl. et al., "Perfusion of Autologous Splenic Grafts in Correlation with Specific Immunological Functions An Experimental Study in Pigs," *Eur. Surg. Res.* vol. 19, 53–61 (1987).

Ptasinska–Urbanska, et al., "Intrascleral Introduction of Isolated Allogeneic Chondrocytes Capable of Cartilage Reformation in Rabbits; Possible Procedure in Treatment of Detachment of the Retina," *Exp. Eye Res.*, vol. 24, No. 3, pp. 241–247 (1977).

Redmond, D.E., Jr., et al., "Fetal Neuronal Grafts in Monkeys Given Methyphenyltetrahydropyridine," *The Lancet*, pp. 1125–1127 (May 17, 1986).

Redmond, D.E., Jr., et al., "Transplants of Primate Neurons," Lancet, 2(8514):1046 (Nov. 1, 1986).

Reid, L.M., et al., "Long–term Cultures of Normal Ray Hepatocytes on Liver Biomatrix," Ann. NY Acad. Sci. (1980).

Rhine, et al., "Polymers for Sustained Macromolecule Release: Procedures to Fabricate Reproducible Delivery Systems and Control Release Kinetics," *Journal of Pharmaceutical Sciences*, vol. 69, No. 3 (Mar. 1980).

Rosen, Howard B., et al., "Bioerodible Polymers for Controlled Release Systems," Controlled Release Systems: *Fabrication Technology*, vol. II, Chapter 5, pp. 83–110.

Rosen, Howard B., et al., "Bioerodible Polyanhydrides for Controlled Drug Delivery," 1983 Butterworth & Co. (Publishers) Ltd.

Sapoznikova, et al., "Morphological Changes in Splenic Autografts Following Splenectomy: Experimental and clinical Microscopy of Vascular Casts," *Virchows Arch*. vol. 409, 325–334 (1986).

Sasaki, "Neovascularization in the Splenic Autograft Transplanted into Rat Omentum as Studied by Scanning Electron Microscopy of Vascular Casts," *Virchows Arch*. vol. 409, 325–334 (1986).

Sawada, N., et al., "Effects of Extracellular Matrix Components of the Growth and Differentiation of Cultured Rat Hepatocytes," *In Vitro Cellular & Development Biology*, vol. 23, No. 4, pp. 267–273 (Apr. 1987).

Schmeck, Harold M., "Doctors Try to Capitalize on the Liver's Ability to Regenerater Itself," *The New York Times Medical Science* (May 16, 1989).

Schubert, et al., "Multiple Influences of a Heparin–Binding Growth Factor on Neuronal Development," *J. Cell. Biol.* 104, 635–643 (1987).

Seckel, B.R., et al., "Nerve Regeneration Through Synthetic Biodegradable Nerve Guides: Regulation by the Target Organ," *Plast Reconstr. Surg.*, 74(2):173–81 (Aug. 1974).

Selden, et al., "The Pulmonary Vascular Bed as a Site for Implantation of Isolated Liver Cells in Inbred Rats," *Transplant* vol. 38, No. 1, pp. 81–83 (Jul. 1984).

Shine, H.D., et al., "Cultured Peripheral Nervous System Cells Support Peripheral Nerve Regeneration Through Tubes in the Absence of Distal Nerve Stump," *J. Neurosci. Res.*, 14(4):393–401 (1985).

Siegel, Ronald A., et al., "Controlled Release of Polypeptides and Other Macromolecules," *Pharmaceutical Research 1984*, pp. 2–10.

Sirica, Alphonse, et al., "Fetal Phenotypic Expression by Adult Rat Hepatocytes on Collagen Gel/Nylon Meshes," *Proc. National Academy Science USA*, vol. 76, No. 1, pp. 283–287 (Jan. 1979).

Sirica, Alphonse, et al., "Use of Primary Cultures of Adult Rat Hepatocytes on Collagen Gel–Nylon Mesh to Evaluate Carcinogen–Induced Unscheduled DNA Synthesis," *Cancer Research*, 40, 3259–3267 (Sep. 1980).

Sladek, J.R., Jr., et al., "Reversal of Parkinsonism by Fetal Nerve Cell Transplants in Primate Brain," *Annals of the New York Academy of Sciences*, vol. 495, pp. 641–657 (New York 1987).

Sladek, J.R., Jr., et al. ,"Survival and Growth of Fetal Catecholamine Neurons Transplanted into Primate Brain," *Brain Res. Bull.*, 17(6):809–18 (Dec. 1986).

Sladek, John R., Jr., et al., "Neural Transplantation: A Call for Patience Rather Than Patients," *Science*, vol. 240, pp. 386–388 (Jun. 10, 1988).

Sladek, John R., Jr., et al., "Transplantation of Fetal Dopamine Neurons in Primate Brain Reverses MPTP Induced Parkinsonism," *Progress i Brain Research*, vol. 71, pp. 309–323 (1987).

Sommer, et al., "Hepatocellular Transplantation for Treatment of D–Gelactosamine–Induced Acute Liver Failure in Rats," *Transplant. Proc.* 11, 578–584 (1979).

Strom, et al., "Isolation, Culture, and Transplantation of Human Hepatocytes," JNCI 68, No. 5, 771–778 (1982).

Sudhakaran, P.R., et al., "Modulation of Protein Synthesis and Secretion by Substratum in Primary Cultures of Ray Hepatocytes," *Exper. Cell Res.* 167 (1986) 505–516.

Sullivan, Walter, "Spinal Injury Research Yields a Glimmer of Hope," *The New York Times*, (Jul. 14, 1987).

Sutherland, et al., "Hepatocellular Transplantation in Acute Liver Failure," *Surgery 82*, 124–132 (Jul. 1977).

Tavassoli, Mehdi, et al., "Studies on Regeneration of Heterotopic Splenic Autotransplants," *Blood*, vol. 41, No. 5, pp. 701–709 (May 1973).

Thompson, John A., et al., "Heparin–Binding Growth Factor 1 Induces the Formation of Organoid Neovascular Structures In Vivo," *Proc. Natl. Acad. Sci. U.S.A.,* vol. 86, pp 7928–7932 (Oct. 1989).

Thompson, J.A., et al., "Implantable Bioreactors: Modern Concepts of Gene Therapy," *Current Communications in Molecular Biology*, Daniel Marshak, et al., editors, pp. 143–147 (Cold Spring Harbor Laboratory, 1989).

Thuroff, et al., "Cultured Rabbit Vesical Smooth Muscle Cells for Lining of Dissolvable Synthetic Prosthesis," *Urology* 21(2), 155–158 (1983).

Tomomura, Akito, et al., "The Control of DNA Synthesis in Primary Cultures of Hepatocytes From Adult and Young Rats: Interactions of Extracellular Matrix Components, Epidermal Growth Factor, and the Cell Cycle," ©1987 Alan R. Liss, Inc.

Unipoint Industries, Inc., "Polyvinyl Alcohol Foam for Surgical and Industrial Use," Product Review.

UNOS Update, "National Cooperative Transplantation Study Completed," vol. 7, Issue 10 (Oct./Nov. 1991).

Upton, J., "Neocartilage Derived from Transplanted Perichondrium: What Is It?" *Plastic and Reconstructive Surgery* 68(2), 166–174 (1981).

Vacanti, J.P. et al., "Selective Cell Transplantation using Bioabsorbable Artificial Polymers as Matrices," *Journal Pediatric Surgery*, vol. 23, No. 1, pp. 3–9 (Jan. 1988).

Vacanti, Joseph P., "Beyond Transplantation," Arch, Surgery, vol. 123, 545–549 (May 1988).

Vargo, Rita, et al., "Infection as a Complication of Liver Transplant," Critical Care Nurse, vol. 9, No. 4, pp. 52–62.

Vija, J., et al., "UV–Induced DNA Excision Repair in Rat Fibroblasts During Immortalization and Terminal Differentiation In Vitro," *Exp. Cell Res.* 167 (1986) 517–530.

Vroeman, et al., "Hepatocyte Transplantation for Enzyme Deficiency Disease in Congenic Rats," *Tranplantation* 42, 130–135 (1986).

Wozney, J.M., et al., "Novel Regulators of Bone Formation: Molecular Clones and Activities," *Science* 242, 1528–1534 (Dec. 16, 1988).

Yannas, et al., "Suppression of In Vivo Degradability and of Immunogenicity of Collagen by Reaction with Glycosaminoglycans," *Polym. Prepr. Am. Chem. Soc. Div. Polym. Chem.*, 16(2), 209–214 (1975).

Yannas, et al., "Design of an Artificial Skin," *J. Biomed. Mater. Res. 14*, 65–81 (1980).

Yannas, I.V., et al., "Wound Tissue Can Utilize a Polymeric Template to Synthesize a Functional Extension of Skin," *Science*, 215, 174–176 (1982).

Yannas, "What Criteria Should be Used for Designing Artificial Skin Replacements and How Well do the Current Grafting Materials Meet These Criteris," *J. of Trauma* 24(9), S29–S39 (1984).

Yannas, et al., "Polymeric Template Facilitates Regeneration of Sciatic Nerve Across 15MM," *Polym. Material Sci. Eng.* 53, 216–218 (1985).

Yannas, et al., "Artificial Skin: A Fifth Route to Organ Repair and Replacement," Iss. Polym. Biomaterial 106, 221–230 (1986).

Yannas, et al., "Regeneration of Sciatic Nerve Across 15mm Gap By Use of a Polymeric Template," Polym. Sci. Technol. Iss. *Adv. Biomed. Polymer* 35, 1–9 (Plenum 1987).

Naughton, B.A., et al., "Granulopoiesis and Colony Stimulating Factor Production in Regerating Liver," *Experimental Hematology*, vol. 10, No. 5, pp. 451–458 (May 1982).

Naughton, B.A., et al., "Long–Term Growth of Rat Bone Marrow Cells in a Three–Dimensional Matrix," The Anatomical Record, vol. 218, No. 1, p. 97A (May 1987).

Naughton, G.K., et al., "Erythropoietin Production by Macrophages in the Regenerating Liver," Journal of Surgical Oncology, 30:184–197 (1985).

* cited by examiner

SEEDING PARENCHYMAL CELLS INTO COMPRESSION RESISTANT POROUS SCAFFOLD AFTER VASCULARIZING IN VIVO

This application is a continuation of application Ser. No. 08/065,452, filed May 21, 1993, now abandoned, which is a continuation of application Ser. No. 07/785,021, filed Oct. 30, 1991, now abandoned, which is a continuation-in-part of application Ser. No. 07/401,640, filed Aug. 30, 1989, now abandoned, which is a continuation of application Ser. No. 06/933,018 filed Nov. 20, 1986, now abandoned; A continuation-in-part of application Ser. No. 07/679,177, filed Mar. 26, 1991, now abandoned, which is a continuation of application Ser. No. 07/401,648, filed Aug. 30, 1989, now abandoned, which is a continuation of application Ser. No. 07/123,579, filed Nov. 20, 1987, now abandoned, which is continuation-in-part of application Ser. No. 06/933,018, filed Nov. 20, 1986, now abandoned; A continuation-in-part of application Ser. No. 07/680,608, filed Apr. 1, 1991, now abandoned, which is a continuation of application Ser. No. 07/343,158, filed Apr. 25, 1989, now abandoned, which is a continuation-in-part of application Ser. No. 07/123,579, filed Nov. 20, 1987, now abandoned, which is a continuation-in-part of application Ser. No. 06/933,018 filed Nov. 20, 1986, now abandoned; A continuation-in-part of application Ser. No. 07/514,171, filed Apr. 25, 1990, now abandoned, which is a continuation-in-part of application Ser. No. 07/343,158, filed Apr. 25, 1989, now abandoned, which is a continuation-in-part of application Ser. No. 07/123,579, filed Nov. 20, 1987, now abandoned, which is a continuation-in-part of application Ser. No. 06/933,018, filed Nov. 20, 1986, now abandoned.

The United States Government has rights in this invention by virtue of NIH grant, No. 6M 26698.

BACKGROUND OF THE INVENTION

1. Field of the Invention

This invention is generally in the field of medicine and cell culture, and in particular in the area of implantable organs formed on biocompatible artificial matrices.

2. Background of the Invention

Loss of organ function can result from congenital defects, injury or disease. Many times treatment with drugs or surgery is not in itself sufficient and the patient dies or is severely disabled. One approach for treatment has been to transplant donor organs or tissue into the patient. Drugs such as cyclosporin can be used to prevent tissue rejection. However, there is a tremendous shortage of donor organs, most of which must come from a recently deceased individual.

There have been a number of attempts to culture dissociated tissue and implant the cells directly into the body. For example, transplantation of pancreatic tissue, either as a whole organ or as a segment of an organ, into the diabetic patient has been attempted. Serum glucose appears to be controlled in a more physiological manner using this technique and the progression of complications is thereby slowed. An earlier approach which was not successful in achieving long-term benefits was the transplantation of islet cells through injection of isolated clusters of islet cells into the portal circulation, with implantation in the vascular bed of the liver. More recent methods have included encapsulation of pancreatic beta cells to prevent immune attack by the host and injection of fetal beta cells beneath the capsule of the kidney. Although there is evidence of short term function, long term results have been less satisfactory (D. E. R. Sutherland, *Diabetologia* 20, 161–185 (1981); D.E.R. Sutherland, *Diabetologia* 20, 435–500 (1981)). Currently whole organ pancreatic transplantation is the preferred treatment.

One of the problems with implanting dissociated cells into the body is that they do not form three dimensional structures and the cells are lost by phagocytosis and attrition. One approach to overcome this problem is wherein cells are encapsulated within spheres, then implanted. While this method can sometimes maintain viable functioning cells, the cells do not form organs or structures and rarely result in long term survival and replication of the encapsulated cells. Most cells have a requirement for attachment to a surface in order to replicate and to function.

The first attempts to culture cells on a matrix for use as artificial skin, which requires formation of a thin three dimensional structure, were described by Yannas and Bell in a series of publications, for example, U.S. Pat. Nos. 4,485, 097; 4,485,096; 4,546,500; 4,060,081; 4,280,954; 4,458, 678; and 4,505,266. They used collagen type structures which were seeded with cells, then placed over the denuded area. A problem with the use of the collagen matrices was that the rate of degradation is not well controlled. Another problem was that cells implanted into the interior of thick pieces of the collagen matrix failed to survive.

One method for forming artificial skin by seeding a fibrous lattice with epidermal cells is described in U.S. Pat. No. 4,485,097 to Bell, which discloses a hydrated collagen lattice that, in combination with contractile agents such as platelets and fibroblasts and cells such as keratinocytes, is used to produce a skin-equivalent. U.S. Pat. No. 4,060,081, to Yannas et al. discloses a multilayer membrane useful as synthetic skin which is formed from an insoluble non-immunogenic material which is nondegradable in the presence of body fluids and enzymes, such as cross-linked composites of collagen and a mucopolysaccharide, overlaid with a non-toxic material such as a synthetic polymer for controlling the moisture flux of the overall membrane. U.S. Pat. No. 4,458,678 to Yannas et al. discloses a process for making a skin-equivalent material wherein a fibrous lattice formed from collagen cross-linked with glycosaminoglycan is seeded with epidermal cells.

A disadvantage to the first two methods is that the matrix is formed of a "permanent" synthetic polymer. U.S. Pat. No. 4,458,678 has a feature that neither of the two prior patents has, a biodegradable matrix which can be formed of any shape, using the appropriate cells to produce an organ such as the skin. Unfortunately, there is a lack of control over the composition and configuration of the latter matrices since they are primarily based on collagen. Further, since collagen is degraded by enzymatic action as well as over time by hydrolysis, the degradation is quite variable.

U.S. Pat. No. 4,520,821 to Schmidt describes a similar approach that was used to make linings to repair defects in the urinary tract. Epithelial cells were implanted onto synthetic matrices, where they formed a new tubular lining as the matrix degraded. The matrix served a two fold purpose—to retain liquid while the cells replicated, and to hold and guide the cells as they In U.S. Ser. No. 06/933,018, filed Nov. 20, 1986, now abandoned, entitled "Chimeric Neomorphogenesis of Organs Using Artificial Matrices" filed Nov. 20, 1986 by Joseph P. Vacanti and Robert S. Langer, a method of culturing dissociated cells on biocompatible, biodegradable matrices for subsequent implantation into the body was described. This method was designed to overcome a major problem with previous attempts to culture cells to form three dimensional structures having a diameter of greater than that of skin. Vacanti and Langer recognized that there was a need to have two elements in any matrix used to form organs: adequate structure and surface area to implant a large volume of cells into the body to replace lost function and a matrix formed in a way that allowed adequate diffusion of gases and nutrients throughout the matrix as the cells attached and grew to maintain viability in the absence of vascularization. Once implanted and vascularized, the porosity required for diffusion of the nutrients and gases was no longer critical.

However, even with the method described by Vacanti, the implant was initially constructed in vitro, then implanted. It is clearly desirable to be able to avoid the in vitro step. U.S. Ser. No. 07/343,158, filed Apr. 25, 1989, now abandoned, by Vacanti, et al., describes an approach used to address this problem. Recognizing the need for vascularization to maintain the implant in vitro, first addressed in the 1986 patent application U.S. Ser. No. 06/933,018, et al., the implant was seeded in vitro then immediately implanted into a highly vascularized tissue, the mesentery. A drawback with this was that the implant could only be made into this area of the body, and that a number of thin implants had to be used to achieve the requisite number of cells.

It is therefore an object of the present invention to provide an implant containing the requisite number of cells to replace lost organ function.

It is a further object of the present invention to provide a biocompatible, polymeric implant which can be implanted with cells without prior in vitro culturing and then degrades at a controlled rate over a period of time as the implanted cells replicate and form an organ structure.

SUMMARY OF THE INVENTION

A method is disclosed whereby cells having a desired function are seeded on and into biocompatible, biodegradable or non-degradable polymer scaffolding, previously implanted in a patient and infiltrated with blood vessels and connective tissue, to produce a functional organ equivalent. The resulting organoid is a chimera formed of parenchymal elements of the donated tissue and vascular and matrix elements of the host.

The matrix should be a pliable, non-toxic, injectable porous template for vascular ingrowth. The pore size, usually between approximately 100 and 300 microns, should allow vascular and connective tissue ingrowth throughout approximately 10 to 90% of the matrix, and the injection of cells such as hepatocytes without damage to the cells or patient. The introduced cells attach to the connective tissue and are fed by the blood vessels. The preferred material for forming the matrix or support structure is a biodegradable synthetic polymer, for example, polyglycolic acid, polylactic acid, polyorthoester, polyanhydride, or copolymers thereof, or a sponge derivatized from polyvinyl alcohol. The elements of these materials can be overlaid with a second material to enhance cell attachment. The polymer matrix must be configured to provide access to ingrowing tissues to form adequate sites for attachment of the required number of cells for viability and function and to allow vascularization and diffusion of nutrients to maintain the cells initially implanted. An advantage of the biodegradable material is that compounds such as angiogenic factors, biologically active compounds which enhance or allow ingrowth of the blood vessels, and lymphatic network or nerve fibers, may be incorporated into the matrix for slow release during degradation of the matrix.

Cells of one or more types can be selected and grown on the matrix. A preferred type of cell is a parenchymal cell such as a hepatocyte, which is difficult to culture under normal conditions. Cells genetically engineered to include genes encoding proteins which would otherwise be absent, such as those resulting from liver protein deficiencies and metabolic defects such as cystic fibrosis, can be implanted with this method.

In the preferred embodiment for implanting cells with a high oxygen requirement such as hepatocytes, the porous implant containing an indwelling catheter is implanted into the mesentery, prevascularized for a period of time, such as five days, and cells injected. In the most preferred embodiment for hepatocytes, immediately prior to polymer implantation portacaval shunts are created to provide trophic stimulatory factors to the implants to enhance replication and function.

DETAILED DESCRIPTION OF THE INVENTION

Figure 1:
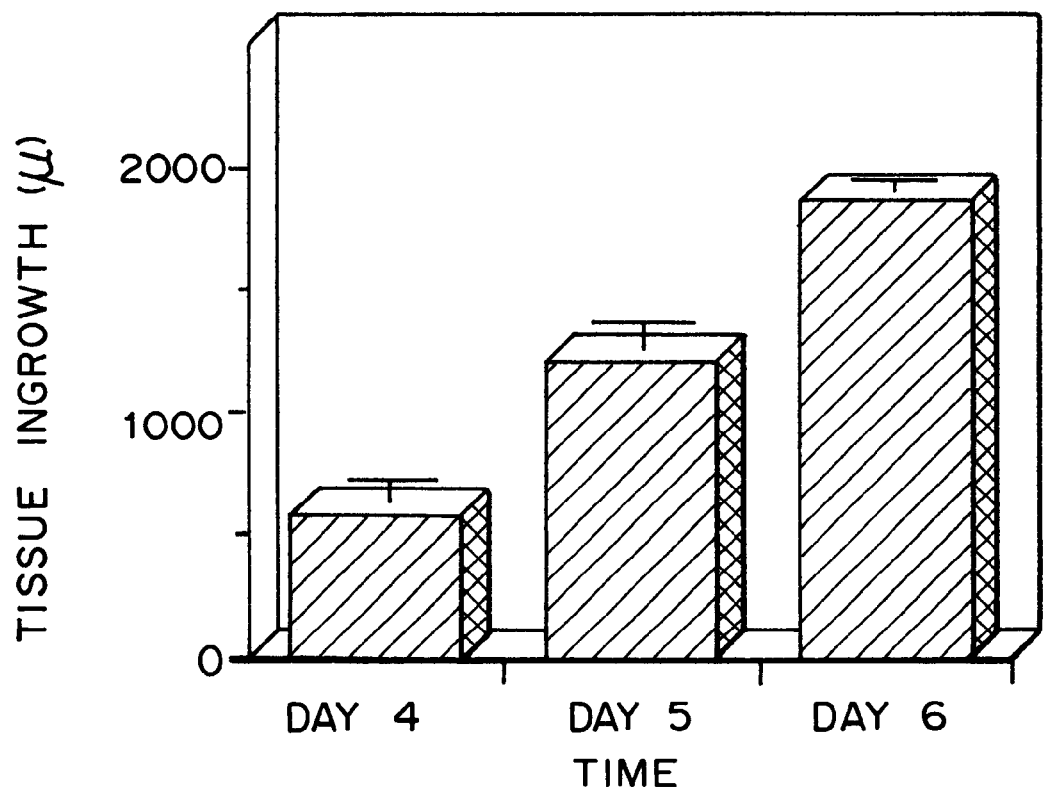
FIG. 1 is the tissue ingrowth ($\mu$) into Ivalon™, at four days, five days, and six days after implantation.

Disclosed herein is a method to provide functional organ equivalents using artificial substrates as scaffolding for cellular transfer and implantation. Cell shape is determined by cytoskeletal components, and attachment to matrix plays an important role in cell division and differentiated function. If dissociated cells are placed into mature tissue as a suspension without cell attachment, they may have difficultly finding attachment sites, achieving polarity, and functioning because they begin without intrinsic organization. This limits the total number of implanted cells which can remain viable to organize, proliferate, and function.

For an organ to be constructed, successfully implanted, and function, the matrices must have sufficient surface area and exposure to nutrients such that cellular growth and differentiation can occur prior to the ingrowth of blood vessels following implantation. The time required for successful implantation and growth of the cells within the matrix is greatly reduced if the area into which the matrix is implanted is prevascularized. After implantation, the configuration must allow for diffusion of nutrients and waste products and for continued blood vessel ingrowth as cell proliferation occurs.

Cells can either be implanted after seeding onto a matrix or injected into a matrix already implanted at the desired site. The latter has the advantage that the matrix can be used to prevascularize the site.

Design and Construction of Scaffolding

The design and construction of the scaffolding is of primary importance. The matrix should be a pliable, nontoxic, injectable porous template for vascular ingrowth. The pores should allow vascular ingrowth and the injection of cells such as hepatocytes without damage to the cells or patient. These are generally interconnected pores in the range of between approximately 100 and 300 microns. The matrix should be shaped to maximize surface area, to allow adequate diffusion of nutrients and growth factors to the cells and to allow the ingrowth of new blood vessels and connective tissue. At the present time, a porous structure that is resistant to compression is preferred.

In the preferred embodiment, the matrix is formed of a bioabsorbable, or biodegradable, synthetic polymer such as a polyanhydride, polyorthoester, polylactic acid, polyglycolic acid, and copolymers or blends thereof. Non-degradable materials can also be used to form the matrix. Examples of suitable materials include ethylene vinyl acetate, derivatives of polyvinyl alcohol, teflon, and nylon. The preferred non-degradable materials are a polyvinyl alcohol sponge, or alkylation, and acylation derivatives thereof, including esters. A non-absorbable polyvinyl alcohol sponge is available commercially as Ivalon™, from Unipoint Industries. Methods for making this material are described in U.S. Pat. No. 2,609,347 to Wilson; U.S. Pat. No. 2,653,917 to Hammon, U.S. Pat. No. 2,659,935 to Hammon, U.S. Pat. No. 2,664,366 to Wilson, U.S. Pat. No. 2,664,367 to Wilson, and U.S. Pat. No. 2,846,407 to Wilson, the teachings of which are incorporated by reference herein. Collagen can be used, but is not as controllable and is not preferred. These materials are all commercially available. Non-biodegradable polymer materials can be used, depending on the ultimate disposition of the growing cells, including polymethacrylate and silicon polymers.

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, mixtures thereof, and other materials known to those skilled in the art of cell culture.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

In a preferred embodiment, the matrix contains catheters for injection of the cells into the interior of the matrix after implantation and ingrowth of vascular and connective tissue. Catheters formed of medical grade silastic tubing of different diameters and of differing exit ports to allow even distribution of cells throughout the matrix, as described in the following examples, are particularly useful. Other methods can also be used, such as molding into the matrix distribution channels from the exterior into various parts of the interior of the matrix, or direct injection of cells through needles into interconnected pores within the matrix.

Preparation of Cells for Implantation

Cells can be obtained directed from a donor organ, from cell culture of cells from a donor organ, or from established cell culture lines. In the preferred embodiments, cells are obtained directly from a donor organ, washed and implanted directly into a pre-implanted, pre-vascularized matrix. The cells are cultured using techniques known to those skilled in the art of tissue culture.

In one variation of the method using a single matrix for attachment of one or more cell lines, the scaffolding is constructed such that initial cell attachment and growth occur separately within the matrix for each population. Alternatively, a unitary scaffolding may be formed of different materials to optimize attachment of various types of cells at specific locations. Attachment is a function of both the type of cell and matrix composition. Cell attachment and viability can be assessed using scanning electron microscopy, histology, and quantitative assessment with radioisotopes.

Although the presently preferred embodiment is to utilize a single matrix implanted into a host, there are situations where it may be desirable to use more than one matrix, each implanted at the most optimum time for growth of the attached cells to form a functioning three-dimensional organ structure from the different matrices.

The function of the implanted cells, both in vitro as well as in vivo, must be determined. In vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. Studies using labelled glucose as well as studies using protein assays can be performed to quantitate cell mass on the polymer scaffolds. These studies of cell mass can then be correlated with cell functional studies to determine what the appropriate cell mass is.

Methods of Implantation

The technique described herein can be used for delivery of many different cell types to achieve different tissue structures. For example, islet cells of the pancrease may be delivered in a similar fashion to that specifically used to implant hepatocytes, to achieve glucose regulation by appropriate secretion of insulin to cure diabetes. Other endocrine tissues can also be implanted. The matrix may be implanted in many different areas of the body to suit a particular application. Sites other than the mesentery for hepatocyte injection in implantation include subcutaneous tissue, retroperitoneum, properitoneal space, and intramuscular space.

Implantation into these sites may also be accompanied by portacaval shunting and hepatectomy, using standard surgical procedures. The need for these additional procedures depends on the particular clinical situation in which hepatocyte delivery is necessary. For example, if signals to activate regeneration of hepatocytes are occurring in the patient from his underlying liver disease, no hepatectomy would be necessary. Similarly, if there is significant portosystemic shunting through collateral channels as part of liver disease, no portacaval shunt would be necessary to stimulate regeneration of the graft. In most other applications, there would be no need for portacaval shunting or hepatectomy.

The methods using polymeric implants and prevascularization, as described above, will be further understood by reference to the following examples.

EXAMPLE 1

Determination of Factors Required for in Vivo Survival of Cells

Methods described in prior patent applications were used to determine the relative importance of various factors in survival of the cells following implantation. Hepatocytes were studied immediately after isolation, when placed on polymer constructs in vitro, and at various time points starting at time zero after implantation. Standard hepatocyte isolation techniques were used. Implantation consisted of attaching cells of varying densities to a polymer fiber complex in vitro and then implantation of this complex. The intestinal mesentery was the implantation site.

The results demonstrated that it was possible to achieve consistently high viabilities of well functioning hepatocytes pre-implantation. Viability ranged from 85–90%. Routine Percoll separation was found to improve viability. It was also determined that the viability and function remained high on the polymer constructs in vitro. By contrast, using the prior art method, there was immediate massive loss of cell viability and function after implantation. Morphometric approaches to quantitative analysis of these fiber complexes were performed but were difficult since viable cells were so rare in the graft. Quantitative estimates of cell loss were between 95–97%. Histologically, there seemed to be stability of the remaining cell masses after the first 24–28 hours with long term engraftment and function of these cells out to one year as documented by in situ histochemical staining for albumin. The hepatocytes remained in clusters varying between 100–250 microns in diameter. These clusters were consistent in appearance independent of cell density application and location of implantation site. The clusters always were predominant in regions closest to the native tissue and blood vessels. These observations suggested that diffusion limitations, especially of oxygen, were the most likely contributors of hepatocyte death. In contrast, similar experiments using chondrocytes to make new cartilage were highly successful with formation of homogeneous plates of cartilage, again suggesting that the particular sensitivity of the hepatocyte to hypoxic damage was the problem.

EXAMPLE 2

Prevascularization and Implantation of Cells on Polylactic Acid and Polyglycolic Acid Matrices

Design of Polymers

Silastic tubing (0.3 mm ID) was divided into 2.5 inch lengths. One end was sealed and 0.25 mm holes cut into the tubing. These injection catheters were introduced centrally into 1 cm discs of polyvinyl alcohol foam (Ivalon™, Unipoint Indust.) with a 5 mm thickness. These devices were then sterilized for implantation.

Animal Implantation

200–250 g Fisher 344 rats were anaesthetized with methoxyflurane and the abdomen prepped. A midline incision was made and the mesentery carefully laid out on sterile gauze. The polymer was then placed onto the mesentery which was then folded back on the device to encase it. The polymer was fixed in place with a single 6-0 Prolene™ (Ethicon) suture. At this point an incision was made in the lateral abdominal wall and the injection catheter led through the muscle to a subcutaneous pocket and fixed. The abdomen was closed and skin approximated. This could then be accessed later for atraumatic introduction of hepatocytes.

Histologic Examination

After appropriate formalin fixation, each prevascularized implant was sectioned at four predetermined sites perpendicular to the axis of the injection catheter. Hematoxylin and Eosin (H&E) staining was performed and the sections evaluated for vascularity, tissue ingrowth and viable hepatocyte area. Quantification of these parameters was carried out using a model 3000 Image Analyser.

Hepatocyte Isolation

Hepatocytes were isolated using a modification of the Seglan technique. A syngeneic donor Fisher 344, 200–250 g rat was anaesthetized with methoxyflurane. The liver was exposed and the IVC cannulated with a 16 g angiocath. A 6 minute perfusion with calcium free buffered perfusate at 38° C. was carried out. This was followed by perfusion with 0.05% Collagenase D (Boehringer Mannheim) in a 0.05 M calcium chloride containing buffer until adequate hepatocyte dissociation was achieved. The hepatocytes were then purified using Percoll density centrifugation. Viability was determined by Trypan Blue nuclear exclusion.

Hepatocyte Injection

Hepatocytes were suspended in Williams E medium (Gibco) at $1\times10^7$ and $2\times10^7$ viable cells/cc. Following 5 days of polymer prevascularization, rats receiving cell injections were anaesthetized, the subcutaneous injection catheter exposed and 0.5 cc of cell suspension was injected and animals harvested either immediately after injection, 1 day after injection or 7 days following injection. Catheters were replaced in the subcutaneous pocket and skin reapproximated.

Results

Tissue Ingrowth

Devices were harvested following 1 to 14 days of prevascularization. Tissue ingrowth occurred at a very consistent rate over time. Between day 1 and day 3 fibrin clot deposition with increasing cellularity was noted. There was no evidence of tissue organization or vascular ingrowth noted during this time. At day 4 organized tissue, as well as capillaries, could be noted extending into the interconnected interstices of the device. Tissue ingrowth was symmetric from both sides of the device until confluence was reached at day 7 of prevascularization. The rate of tissue ingrowth was constant at 604 µm/day (range 575–627 µm/day) between days 4 and 7, as shown in FIG. 1.

It appears to be essential that spaces are consistently maintained between the polymer and the tissue. It is this space which create channels for the injection and implantation of hepatocytes.

Vascularity

Figure 2A:
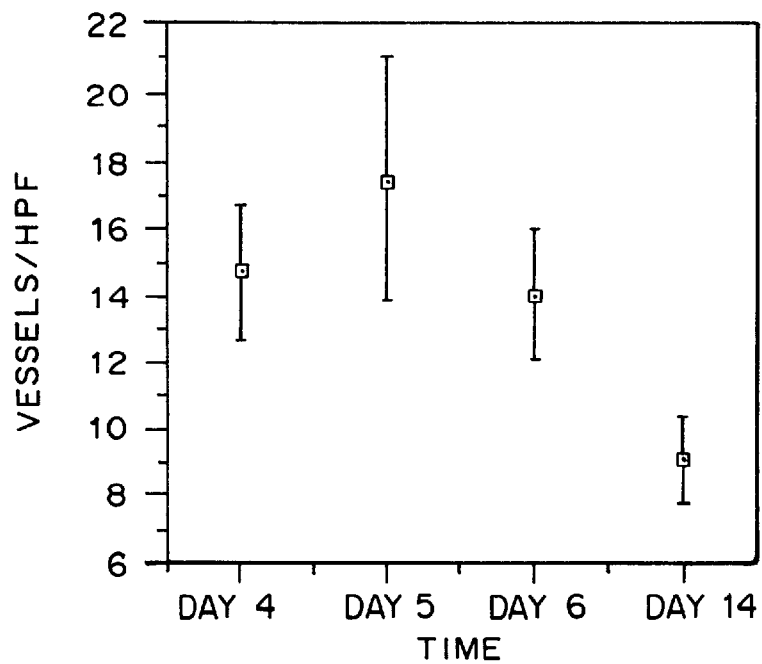
FIG. 2a is the vascularity of Ivalon™ over time, vessels/hepatocytes per field (HPF) 2a at four days, five days, six days, and fourteen days.
Figure 2B:
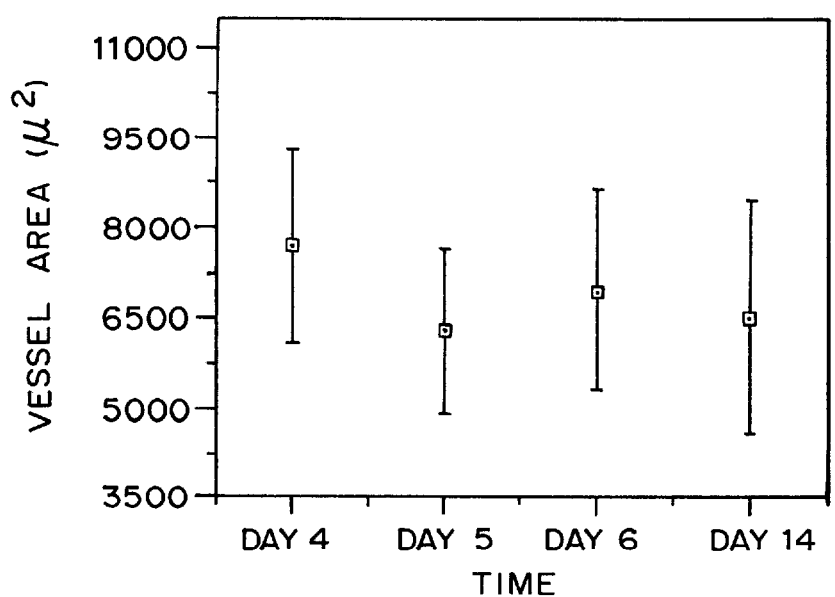
FIG. 2b is the vascularity of Ivalon™ over time, vessel area ($\mu^2$) at four days, five days, six days, and fourteen days.

Vascularity was assessed in two ways. First, the vessel number per unit area was determined at multiple preselected sites within the polymer and an average obtained. Second, the vessel area within these same fields was determined. The field which was quantified was the most central extent of organized tissue ingrowth. The results are depicted graphically in FIGS. 2a and b. Once tissue organization occurred, vessel number/HPF reached a maximal density of 17 at day 5 of prevascularization before declining to 9 vessels/HPF by day 14. This was in contrast to vessel area which remained constant over time, indicating a progression from smaller to larger vessels over this period.

Hepatocyte Distribution and Survival

The hepatocytes distributed themselves evenly throughout the polymer at the time of cell injection. Viable cells became increasingly localized to the interface of the mesentery and polymer over time. Histologically it was demonstrated that the cells initially viable require attachment to the fibrovascular tissue network to survive. Those not in contact become nonviable within 24 hours. By one week hepatocytes were limited to the outer edge of the device. The cells did not appear to thrive in the central portion of the polymer even following attachment to the tissue ingrowth. Remodeling occurred and the cells which did engraft became incorporated into the fibrovascular tissue as islands of 4–5 cells or as a 2–3 cell layer sheet around the outer margins of the polymer. Hepatocyte area within the polymer was examined to assess survival. A 40% decrease in viable hepatocyte area over the first 24 hours with a gradual decrease to 25% of initial hepatocyte area by 1 week was shown. Examination of implants at 4 months demonstrated a continued fall in hepatocyte area to between 5 and 10% of cells implanted at time 0. Increasing the number of cells injected by 100% provided a 100% increase in viable hepatocyte area with a proportional decrease in area over time.

EXAMPLE 3

Implantation of Hepatocytes using Porous Polyvinyl Alcohol Implants

A number of studies, including example 1, indicated there was a massive loss of hepatocytes using the technique of attaching hepatocytes to polymer fibers of polyglycolicacid in cell culture and then implanting these polymer cell constructs into the mesentery of the intestine. To approach these problems, new assays to assess cell viability and function before, during, and after cell implantation, alternative cell isolation techniques, new materials to improve cell viability, and systems of prevascularization to improve vascularized surface area for implantation were developed. As a result of these efforts, it was determined that the major cause of cell death was related to variables at the time of implantation. Most cell death occurred within the first six hours after implantation. 95–97% of hepatocytes were lost in this early period after implantation.

Morphometric techniques to analyze tissue sections of the implants in vivo were developed. This analysis in vivo was coupled with the development of quantitative "Northern" blot analysis to measure total RNA as well as liver-specific albumin mRNA within the implant. These in vivo observations could be compared to in vitro RNA analysis of cells on polymer as well as measurement of albumin production using gel electrophoresis. In vitro and in vivo analysis measuring viability using MTT(30)4,5-dimethyl thiazol-2-yl(-2,5-diphenyl tetrazolium bromide), was used in the assay. This biochemical assay was used as a non specific marker of cell viability and was compared to acid phosphatase measurements.

A system utilizing porous polymers of polyvinyl alcohol allowing successful transplantation, defined as long term engraftment and organization of hepatocytes and biliary duct-like structures, was developed. Cell survival was increased to the 60–70% range by developing polymer systems allowing prevascularization into sponge like porous materials. The efficiency of delivery of cells is estimated to be between 40 and 60% at 24 to 28 hours after implantation. The results indicate that the strategy of prevascularization into a sponge like geometry with secondary introduction of hepatocytes significantly decreases early cell loss.

Gunn rats (150–250 g) were anaesthetized and end to side portacaval shunts created. 1.5×1.5 cm polymer sponges with central multiport silastic tubes for cell injection were placed in mesenteric envelopes or subcutaneous pockets (n=20). After 5 days of prevascularization, hepatocytes were isolated from a syngeneic Wistar rat by collagenase perfusion. $1 \times 10^7$ hepatocytes were injected. Three days after engraftment a 70% hepatectomy was performed and the implants serially evaluated by H&E sectioning out to six months. Individual cross-sectional areas of ductal structures in native liver, heterotopic transplanted grafts and the implants were compared by morphometric quantification. Analysis of variance was used to assess statistical significance.

Hepatocyte engraftment and reorganization occurred in all implants out through six months. Organized nodules of up to 1 mm were identified with hepatocytes arranged in plates. 30% of the implants at 4 and 6 months (n=10) contained tubular structures lined by cuboidal epithelium with a histologic appearance similar to those in heterotopic transplants with bile duct hyperplasia. The area of these ducts was compared to interlobular ducts, the smallest biliary structures with cuboidal epithelium, in heterotopic grafts and native liver. The ducts in the implants had a mean area of 745 $\mu^2 \pm 47$, the hyperplastic ducts within the heterotopic transplant, 815 $\mu^2 \pm 41$ (p=0.3), while those with comparable morphology from the portal triad of native liver had a mean of 1360 $\mu^2 + 105$ (p<0.001).

Both long term engraftment and development of ductal structures within organized nodules of hepatic tissue in both mesenteric and subcutaneous hepatocyte implants was demonstrated. These structures, which are morphologically and morphometrically similar to those seen in bile duct hyperplasia in heterotopic liver transplants, represent the first evidence suggestive of bile duct organization following hepatocyte transplantation.

EXAMPLE 4

Comparison of Polymer Fiber Matrices with Polyvinyl Alcohol Sponge Matrices

Empty polymers were implanted to allow fibrovascular ingrowth into the complex before hepatocyte introduction to increase vascularized surface area, thereby allowing shorter diffusion distances for oxygen delivery. Several geometric configurations were tested, including 1) bioabsorbable polymer fibers only, 2) nondegradable polymer fibers, 3) mixtures of degradable as well as nondegradable fibers, 4) cellulose sponges, 5) Ivalon™ sponges.

All of the unsupported fiber complexes were unsuitable for prevascularization for two reasons. First of all, they did not have enough resistance to compression and thus contraction occurred as fibrovascular tissue migrated. This also created a very high resistance to introduction of hepatocytes, whether they were introduced by direct injection or by an indwelling multiport catheter. Direct injection produced bleeding within the interstices of the implant.

A sponge model was then developed since it seemed to have greater resistance to compression and allowed for maintenance of potential spaces. Many studies were performed with both Ivalon™ sponges and the cellulose sponge to determine the time course for vascularization. Good vascular ingrowth occurred in both models. The standard Ivalon™ sponge implant was a disc of one centimeter diameter by 0.3 cm in height. There was good vascular ingrowth by, day 5 and very thorough vascular ingrowth by day 11. The pores were of quite uniform size and all interconnected. A system was designed in which a central multiport catheter was placed into the Ivalon disc so that hepatocytes could be introduced either as a single injection or multiple injections. Although the cellulose sponge allowed for good vascular ingrowth with minimal inflammation, the pores were of very inconsistent size and therefore made it less suitable than the Ivalon™.

Methods

Prevascularized Ivalon Sponge

Ivalon™ sponges were placed into the mesentery of Fischer 344 rats and allowed to prevascularize for varying numbers of days. At designated times hepatocytes were injected through the centrally placed silastic catheter. The concentration of hepatocytes and final volume infused into the sponges were varied. The animals were perfused with formalin at Time 0 and three days after hepatocyte injection. This was chosen based on prior work which has shown fairly consistent cell survival after this point and that the hepatocyte loss occurred over the first 24 hours. The cell/polymer constructs were then sectioned and evaluated for tissue ingrowth, vascularity, hepatocyte distribution and viability. Quantitation of the viable hepatocytes was carried out using morphometric image analysis.

To determine cell number, each implant was divided into four pieces and a section made from each of these. Each of these sections was then examined through three cross sections microscopically and cell area determined. Average cell area and volume were then determined and cell number extrapolated for the volume of the sponge.

RNA Isolation from Polymer Implants

Hepatocytes were isolated by collagenase perfusion and centrifugation through Percoll. Prior to injection into pre-vascularized Ivalon™ sponge, cellular RNA was labeled in suspension with 10 $\mu$Ci/ml$^3$H-uridine. Pre-labeling hepatocyte RNA allows distinction between hepatocyte RNA and that of infiltrating cells. $5 \times 10^6$ labeled hepatocytes were then injected into Ivalon™ sponge as described elsewhere. In previous experiments using polyglycolic acid (PGA), cells were applied to polymer in a tissue culture dish, incubated overnight in 10 $\mu$Ci/ml$^3$H-uridine, and implanted as previously described.

To isolate RNA, implants were removed at time intervals and placed in a guanidinium isothiocyanate lysis solution. Multiple aliquots of this solution were worked through the sponge and combined. The RNA was purified by subsequent phenol-chloroform extractions, and lithium chloride and ethanol precipitations. The final RNA samples were applied to a nitrocellulose filter using a slot blot apparatus (Schleicher and Schuell). Following hybridization with a $^{32}$P-labeled cDNA probe specific for albumin MRNA, the filter was washed and placed on X-ray film. The resulting autoradiograph was scanned with a densitometer to quantitate relative amounts of albumin mRNA in each sample.

Alternatively, RNA samples can be electrophoresed to separate MRNA species, blotted onto nitrocellulose, and probed as usual. This latter procedure is termed "Northern" blot analysis.

Results

Prevascularized Ivalon™ Sponge

Tissue Ingrowth

Infiltrating tissue completely bridged the 3 mm thickness of Ivalon™ in 7 days. The extent of its fibrous and vascular components increase over time. Highly vascular, minimally fibrous tissue was present at 5 days. At this time there were still relatively hypocellular areas centrally in the implant. Tissue became further organized through day 14 with a decrease in potential space for cell implantation.

Distribution of Cells with Injection

Cell distribution remained consistent over the entire time course with an even distribution of cells immediately after injection. Over the three days following injection, cell survival became more predominant at the periphery where the new tissue was more organized.

Hepatocyte Survival

Figure 4:
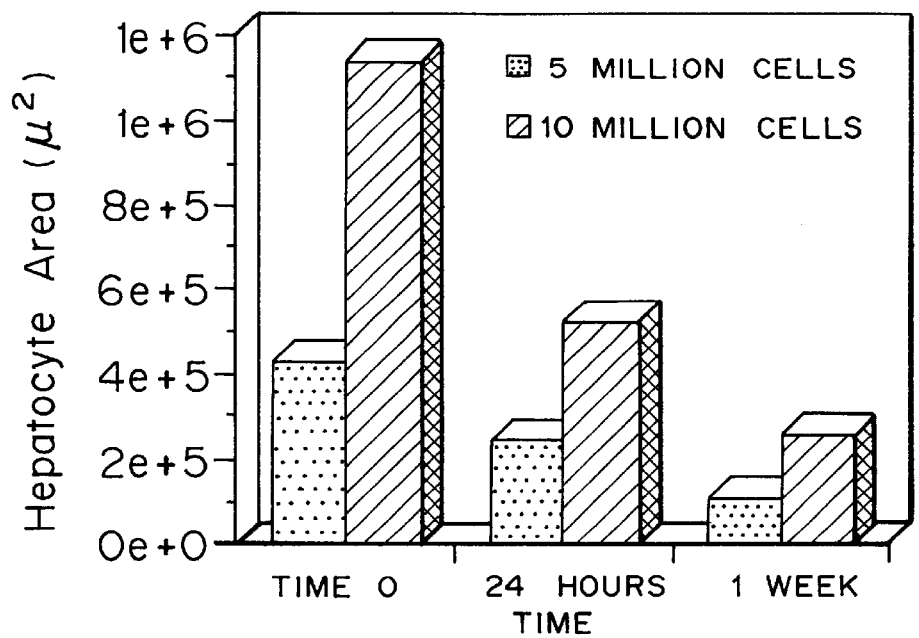
FIG. 4 is a graph of hepatocyte survival in Ivalon™, hepatocyte area ($\mu^2$) at 0 time, 24 hours, and one week for 5 million cells and 10 million cells.

The survival of hepatocytes was determined over a three day time course comparing cell areas of 10–14 fields per section and four sections per sponge. This allowed comparison of cell survival of hepatocytes injected into a similar group of rats from the same hepatocyte isolation. The results are shown in FIG. 4.

In the first group of animals, morphometry revealed an average viable cell area of 3153±645 (S.E.M.at time 0 following injection). At three days, the average viable cell area was 1960±567.

These cell areas correlated to an average cell survival of 62% from day 0 to day 3. Calculating for cell number based on a determined average cell size and sponge volume, $3.6 \times 10^6$ viable hepatocytes are present at day 3.

In a second group of animals, cell survival at time 0 after injection revealed a cell area of 1089±334 with cell area at 24 hours of 1175±445. This represents complete survival over this period within the error of the method.

Total number of viable cells was 1.8 and $1.9 \times 10^6$ cells per sponge, respectively, in these implants.

RNA Isolation from Polymer Implants

PGA and Ivalon™ sponge samples were compared for albumin mRNA levels. In the PGA experiment, four polymer pieces were combined for each timepoint, whereas duplicate sponge samples were processed for each timepoint in the Ivalon™ experiment. Quantitation of slot blot analysis demonstrated a 3-fold, or 97%, decrease in albumin mRNA in hepatocytes on PGA polymer between 0 and 24 hours, consistent with previous results of Northern blot analysis. In contrast, Ivalon™ sponge samples exhibit a 1.6-fold (36%) decrease at 24 hours. Furthermore, the total amount of Ivalon™ RNA obtained is similar from 0 to 24 hours, whereas this also dropped dramatically on PGA polymer. These results indicate that hepatocytes maintain the majority of their function in vivo at the level of albumin gene expression on Ivalon sponge, but not on PGA polymer.

EXAMPLE 5

Effect of Hepatotrophic Stimulation on Graft Survival using Prevascularized Matrices These results indicate that prevascularization of a sponge model of hepatocyte implantation significantly improves cell survival in the first 24 hours after implantation. Further increases in survival can be obtained by using portacaval shunting and hepatectomy, and addition of $O_2$ directly to implanted cells using a temporary implanted tissue perfusion chamber.

Methods

Polymer Implantation

Inbred Lewis rats, 250–350 g (Charles River), were anaesthetized with methoxyflurane. A midline incision was made and the mesentery laid out on a sterile gauze. Ivalon™ (Unipoint Industries) foam discs with a centrally placed silastic injection catheter were fixed into a mesenteric envelope. The injection catheters were led to a distant subcutaneous site. The mesentery with polymer was returned to the abdominal cavity and the incision closed. Animals received a single dose of kefzol 100 at mg/kg.

Portacaval Shunt

Immediately prior to polymer implantation portacaval shunts were created. The pancreaticoduodenal vein was ligated and transected. The portal vein was mobilized from liver hilum to splenic vein with care taken to avoid the hepatic artery. The vena cava was mobilized posteromedially from the left renal vein to the inferior edge of the liver. At this point the portal vein was ligated at the liver hilum and a non-crushing clamp applied at the level of the splenic vein. A partially occluding clamp was applied to the anteromedial surface of the vena cava. A venotomy was created and end to side portacaval shunt constructed with running 8-0 Prolene™ (Ethicon) suture. With adequate flow established, implants were placed as described above.

Hevatocyte Isolation

A modified Seglan technique was used for hepatocyte isolation. Following adequate anaesthesia with methoxyflurane the vena cava was cannulated and the liver perfused retrograde with $Ca\pm\pm$ free saline buffer followed by 0.05% collagenase D (Boeringer Mannheim) saline buffer with 0.05 M CaCl. Perfusion was carried out at 39° C. Once hepatocyte dissociation was adequate, the liver was excised and gentle dissociation in Williams E medium (GIBCO) carried out. Viability was assessed using trypan blue nuclear exclusion as the criteria for viability.

Hepatocytes were then further purified using 87% Percoll centrifugation for density separation. The hepatocyte fraction was then resuspended in Williams E medium at $2\times10^7$ cells/cc. The entire ex vivo isolation was carried out at 4° C.

Hepatocvte Implantation and Hepatectomy

Based on initial studies with hepatocyte injection in prevascularized Ivalon, the polymers were prevascularized for 5 days. This provided optimal tissue and vascular ingrowth for engraftment. Animals were given light metaphane anaesthesia, the injection catheters accessed and hepatocytes injected. $1\times10^7$ cells were injected (0.5 cc) per sponge.

Partial hepatectomy was performed at this point in selected animals with and without PC shunts. Standard 70% hepatectomy was performed.

Evaluation of Implants

Cell polymer constructs were harvested one week after cell injection. They were fixed, sectioned and stained with H&E. Quantification was carried out using a Model 3000 Image analyzer and computer assisted morphometric analysis. Each device was sectioned at four locations in a consistent fashion. Hepatocyte area was quantified along four cross sections of each of the four histologic sections. This provided a consistent means of assessment. Statistical significance was assessed using analysis of variance.

Results

Figure 3:
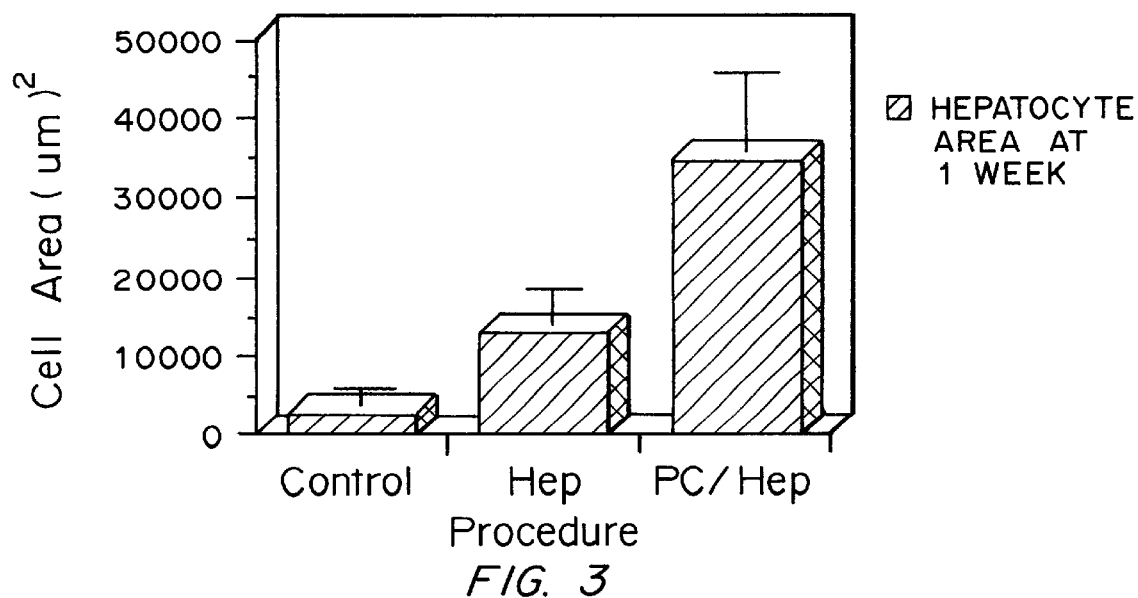
FIG. 3 is a graph of the effect of hepatotrophic stimulation on implant growth, cell area ($\mu m^2$) for control, 70% hepatectomy alone (Hep) and portacaval shunt in combination with 70% hepatectomy (PC/Hep).

Three experimental groups were evaluated. A control group (I) undergoing neither hepatectomy nor portacaval shunt (n=6); a second group (II) which underwent 70% hepatectomy alone (n=6); and the final group (III) which underwent portacaval shunt and 70% hepatectomy (n=6). The cross-sectional hepatocyte area per sponge was 2,643 $\mu^2$ (SEM±1588) for the controls and 12,809 $\mu^2$ (SEM±4074) in animals undergoing hepatectomy alone. For the animals receiving maximal hepatotrophic stimulation with PC shunt and 70% hepatectomy, hepatocyte area reached 34,372 $\mu^2$ (SEM ±9752). This is graphically depicted in FIG. 3.

This increased engraftment in the animals with PC shunt and hepatectomy translates to a twelve fold increase over the controls and almost three fold increase over hepatectomy alone.

Histologic evaluation also revealed significant morphologic differences between the groups which can be summarized as follows. Control animals with no hepatotrophic stimulation only demonstrated engraftment at the outer edge of the polymer near the interface with the mesentery. Based on prior work, this was a progressive phenomenon with cells initially engrafting throughout the interstices of the polymer but with loss of engraftment occurring centrally in the device. The cells also engrafted in 2–3 cell layer laminates. It was noted that, with the addition of partial hepatectomy, cells engrafted with an acinar arrangement in islands 5–6 cell layers thick. Even more striking was the morphology produced with the addition of portacaval shunt. Large aggregates of cells could be demonstrated throughout the polymer. These cells had a much healthier appearance. As well as an acinar arrangement, the cells arranged into laminae with the cord-like appearance of native liver. Another interesting feature was the presence of tubular duct-like structures. Because these structures looked so similar to biliary ducts, morphometric assessment was carried out. The intralobular ducts of native liver and heterotopic grafts were studied as controls for these structures. The histologic appearance of the hepatocellular structures were remarkably similar to those from heterotopic grafts. Morphometric quantification revealed strikingly similar sizes of the ducts from the implants (745 $\mu^2$±47) and the transplants (814 $\mu^2$±40); the native liver (1360 $\mu^2$±97) had ducts which were significantly larger (p<0.001).

Although this invention has been described with reference to specific embodiments, variations and modifications of the method and means for constructing artificial organs by culturing cells on matrices having maximized surface area and exposure to the surrounding nutrient-containing environment will be apparent to those skilled in the art. Such modifications and variations are intended to come within the scope of the appended claims.

We claim:

1. A method enhancing in vivo survival of parenchymal cells in an implanted scaffold comprising:
   a. implanting into the body of a patient a porous three-dimensional scaffold composed of a biocompatible polymer and having generally interconnected pores of between approximately 100 and 300 microns in diameter throughout the scaffold, wherein the pores of the scaffold provide sufficient surface area to the scaffold to permit attachment of an amount of the cells effective to produce functional vascularized organ tissue in vivo, wherein the scaffold is resistant to compression within the patient, to thereby maintain the pore size of the scaffold between approximately 100 and 300 microns, and wherein the structure of the scaffold allows the introduction of cells into the vascularized scaffold without damage to the cells or patient;

b. maintaining the scaffold in the patient until the scaffold is between 10% and 90% vascularized and infiltrated with viable connective tissue; and c. introducing viable parenchymal cells into the vascularized scaffold, wherein survival of the parenchymal cells in the vascularized scaffold is enhanced relative to survival of parenchymal cells in an unvascularized scaffold.

2. A method for enhancing in vivo survival of parenchymal cells in an implanted scaffold comprising:

a. implanting into the body of a patient a porous three-dimensional scaffold composed of a biocompatible polymer having a sponge or foam structure and having generally interconnected pores of between approximately 100 and 300 microns in diameter throughout the scaffold, wherein the pores of the scaffold provide sufficient surface area to the scaffold to permit attachment of an amount of the cells effective to produce functional vascularized organ tissue in vivo, wherein the scaffold is resistant to compression within the patient, to thereby maintain the pore size of the scaffold between approximately 100 and 300 microns, and wherein the structure of the scaffold allows the introduction of cells into the vascularized scaffold without damage to the cells or patient;

b. maintaining the scaffold in the patient until the scaffold is between 10% and 90% vascularized and infiltrated with viable connective tissue; and c. introducing viable parenchymal cells into the vascularized scaffold, wherein survival of the parenchytmal cells in the vascularized scaffold is enhanced relative to survival of parenchytmal cells in an unvascularized scaffold.

3. The method of claim 1 or 2 wherein the cells are introduced into the scaffold by means of a catheter.

4. The method of claim 1 or 2 wherein the scaffold is implanted in a tissue which is selected from the group consisting of the mesentery, subcutaneous tissue, subfascia, and supraperitoneal tissue.

5. The method of claim 1 or 2 further comprising performing a portacaval shunt on the patient.

6. The method of claim 1 or 2 wherein the scaffold is formed from a material selected from the group consisting of polyanhydride, polyorthoester, polyglycolic acid, polylactic acid, copolymers and blends thereof and collagen.

7. The method of claim 1 or 2 further comprising providing in the material forming the scaffold compounds selected from the group consisting of growth factors, compounds stimulating angiogenesis, and immunomodulators.

8. The method of claim 1 or 2 wherein the scaffold contains distribution channels for introduction of the cells.

9. The method of claim 1 or 2 further comprising providing with the scaffold means for introduction of the cells.

10. The method of claim 1 or 2 wherein the cells are hepatocytes.

11. The method of claim 1 or 2 further comprising selecting the cells from the group consisting of parathyroid cells, thyroid cells, cells of the adrenal-hypothalamic-pituitary axis, nerve cells, bone-forming cells, cells forming smooth muscle and cells forming skeletal muscle.

12. The method of claim 1 or 2, wherein the rate of survival of parenchymal cells is at least 40% after 24 hours.

13. The method of claim 1 or 2, wherein the rate of survival of parenchymal cells is in the range of 60–70% after 24 hours.

14. The method of claim 1 or 2, wherein the rate of survival of parenchymal cells is at least 25% after one week.

15. A method for producing a functional vascularized organ tissue in vivo comprising:

a. implanting into a patient a porous three-dimensional scaffold composed of a biocompatible polymer and having generally interconnected pores of between approximately 100 and 300 microns in diameter throughout the scaffold, wherein the pores of the scaffold provide sufficient surface area to the scaffold to permit attachment of an amount of the cells effective to produce functional vascularized organ tissue in vivo, and wherein the scaffold is resistant to compression within the patient, thereby maintaining the pore size of the scaffold to between approximately 100 and 300 microns, and the structure of the scaffold allows the introduction of cells into the vascularized scaffold without damage to the cells or patient;

b. maintaining the scaffold in the patient until the scaffold is between 10% and 90% vascularized and infiltrated with viable connective tissue; and c. introducing viable hepatocytes into the vascularized scaffold.

16. A method for enhancing in vivo survival of hepatocytes in an implanted scaffold comprising:

a. implanting into the body of a patient a porous three-dimensional scaffold composed of a biocompatible polymer having a sponge or foam structure and having generally interconnected pores of between approximately 100 and 300 microns in diameter throughout the scaffold, wherein the pores of the scaffold provide sufficient surface area to the scaffold to permit attachment of an amount of the cells effective to produce functional vascularized organ tissue in vivo, wherein the scaffold is resistant to compression within the patient, to thereby maintain the pore size of the scaffold between approximately 100 and 300 microns, and wherein the structure of the scaffold allows the introduction of cells into the vascularized scaffold without damage to the cells or patient;

b. maintaining the scaffold in the patient until the scaffold is between 10% and 90% vascularized and infiltrated with viable connective tissue; and c. introducing viable hepatocytes into the vascularized scaffold, wherein survival of the hepatocytes in the vascularized scaffold is enhanced relative to survival of hepatocytes in an unvascularized scaffold.

* * * * *